(12) United States Patent
Kotmel et al.

(10) Patent No.: US 8,486,060 B2
(45) Date of Patent: *Jul. 16, 2013

(54) POWER RAMPING DURING RF ABLATION

(75) Inventors: Robert Kotmel, Burlingame, CA (US); Russel M. Sampson, Palo Alto, CA (US); Scott Dennis Taylor, San Martin, CA (US)

(73) Assignee: Cytyc Corporation, Marlborough, MA (US)

(*) Notice: Subject to any disclaimer, the term of this patent is extended or adjusted under 35 U.S.C. 154(b) by 1673 days.

This patent is subject to a terminal disclaimer.

(21) Appl. No.: 11/532,889

(22) Filed: Sep. 18, 2006

(65) Prior Publication Data

US 2008/0071257 A1    Mar. 20, 2008

(51) Int. Cl.
A61B 18/18    (2006.01)
(52) U.S. Cl.
USPC ............................................... 606/38; 606/32
(58) Field of Classification Search
USPC ................................................ 606/34, 38–39
See application file for complete search history.

(56) References Cited

U.S. PATENT DOCUMENTS

| 552,832 A | 1/1896 | Fort |
| 725,731 A | 4/1903 | Linn |
| 1,620,929 A | 3/1927 | Wallerich |
| 1,827,306 A | 10/1931 | Chapman et al. |
| 2,190,383 A | 2/1940 | Newman |
| 2,347,195 A | 4/1944 | Huff |
| 2,466,042 A | 4/1949 | Reich et al. |
| 3,228,398 A | 1/1966 | Leonard et al. |
| 3,324,855 A | 6/1967 | Heimlich |
| 3,645,265 A | 2/1972 | Majzlin |
| 3,840,016 A | 10/1974 | Lindemann |
| 3,845,771 A | 11/1974 | Vise |
| 3,858,586 A | 1/1975 | Lessen et al. |
| 3,877,464 A | 4/1975 | Vermes |

(Continued)

FOREIGN PATENT DOCUMENTS

| DE | 384246 | 10/1923 |
| DE | 22 22 820 | 11/1973 |

(Continued)

OTHER PUBLICATIONS

D.E. Haines et al., "Observations on Electrode-Tissue Interface Temperature and Effect on Electrical Impedance During Radiofrequency Ablation of Ventricular Myocardium," *Circulation*, vol. 82, No. 3, Sep. 1990, pp. 1034-1038.

(Continued)

*Primary Examiner* — Linda Dvorak
*Assistant Examiner* — Jaymi Della
(74) *Attorney, Agent, or Firm* — Robert P. Smith

(57) ABSTRACT

A method for tissue ablation is described. An RF applicator including an electrode carrier with one or more bipolar electrodes thereon is positioned at a target tissue site for tissue ablation. A current at an initial current level is passed through the one or more bipolar electrodes to the target tissue site to apply an initial power density to destroy tissue for an initial time period. A vacuum source in fluid communication with the RF applicator is employed to remove moisture generated during ablation away from the target tissue site. After the initial time period, the power density is ramped up by increasing the current passed through the one or more bipolar electrodes to the target tissue site for a second time period.

13 Claims, 4 Drawing Sheets

U.S. PATENT DOCUMENTS

| | | | |
|---|---|---|---|
| 3,924,628 A | 12/1975 | Droegemueller et al. | |
| 3,948,270 A | 4/1976 | Hasson | |
| 3,967,625 A | 7/1976 | Yoon | |
| 3,971,378 A | 7/1976 | Krantz | |
| 4,022,215 A | 5/1977 | Benson | |
| 4,057,063 A | 11/1977 | Gieles et al. | |
| 4,082,096 A | 4/1978 | Benson | |
| 4,094,320 A | 6/1978 | Newton et al. | |
| 4,114,623 A * | 9/1978 | Meinke et al. | 606/39 |
| 4,158,050 A | 6/1979 | Zipper | |
| 4,185,618 A | 1/1980 | Corey | |
| 4,233,025 A | 11/1980 | Larson et al. | |
| 4,347,842 A | 9/1982 | Beale | |
| 4,359,454 A | 11/1982 | Hoffman | |
| 4,380,238 A | 4/1983 | Colucci et al. | |
| 4,415,288 A | 11/1983 | Gordon et al. | |
| 4,449,528 A | 5/1984 | Auth et al. | |
| 4,465,072 A | 8/1984 | Taheri | |
| 4,492,231 A | 1/1985 | Auth | |
| 4,532,483 A | 7/1985 | Schminke | |
| 4,532,924 A | 8/1985 | Auth et al. | |
| 4,568,326 A | 2/1986 | Rangaswamy | |
| 4,582,057 A | 4/1986 | Auth et al. | |
| 4,601,698 A | 7/1986 | Moulding, Jr. | |
| 4,606,336 A | 8/1986 | Zeluff | |
| 4,628,924 A | 12/1986 | Cimber | |
| 4,662,383 A | 5/1987 | Sogawa et al. | |
| 4,676,258 A | 6/1987 | Inokuchi et al. | |
| 4,691,703 A | 9/1987 | Auth et al. | |
| 4,700,701 A | 10/1987 | Montaldi | |
| 4,739,759 A | 4/1988 | Rexroth et al. | |
| 4,765,331 A | 8/1988 | Petruzzi et al. | |
| 4,788,966 A | 12/1988 | Yoon | |
| 4,807,620 A | 2/1989 | Strul et al. | |
| 4,832,048 A | 5/1989 | Cohen | |
| 4,865,047 A | 9/1989 | Chou et al. | |
| 4,869,268 A | 9/1989 | Yoon | |
| 4,946,440 A | 8/1990 | Hall | |
| 4,949,718 A | 8/1990 | Neuwirth et al. | |
| 4,955,377 A | 9/1990 | Lennox et al. | |
| 4,960,133 A | 10/1990 | Hewson | |
| 4,961,435 A | 10/1990 | Kitagawa et al. | |
| 4,979,948 A | 12/1990 | Geddes et al. | |
| 4,981,465 A | 1/1991 | Ballan et al. | |
| 4,983,177 A | 1/1991 | Wolf | |
| 5,019,076 A * | 5/1991 | Yamanashi et al. | 606/45 |
| 5,026,379 A | 6/1991 | Yoon | |
| 5,047,028 A | 9/1991 | Qian | |
| 5,057,106 A | 10/1991 | Kasevich et al. | |
| 5,065,751 A | 11/1991 | Wolf | |
| 5,078,717 A | 1/1992 | Parins et al. | |
| 5,084,044 A | 1/1992 | Quint | |
| 5,105,808 A | 4/1992 | Neuwirth et al. | |
| 5,147,353 A | 9/1992 | Everett | |
| 5,159,925 A | 11/1992 | Neuwirth et al. | |
| 5,160,334 A | 11/1992 | Billings et al. | |
| 5,178,148 A | 1/1993 | Lacoste et al. | |
| 5,186,181 A | 2/1993 | Franconi et al. | |
| 5,188,122 A | 2/1993 | Phipps et al. | |
| 5,188,602 A | 2/1993 | Nichols | |
| 5,217,473 A | 6/1993 | Yoon | |
| 5,226,908 A | 7/1993 | Yoon | |
| 5,242,437 A | 9/1993 | Everett et al. | |
| 5,248,312 A | 9/1993 | Langberg | |
| 5,263,585 A | 11/1993 | Lawhon et al. | |
| 5,277,201 A | 1/1994 | Stern | |
| 5,308,327 A | 5/1994 | Heaven et al. | |
| 5,318,532 A | 6/1994 | Frassica | |
| 5,322,507 A | 6/1994 | Costello et al. | |
| 5,334,193 A | 8/1994 | Nardella | |
| 5,334,209 A | 8/1994 | Yoon | |
| 5,354,295 A | 10/1994 | Guglielmi et al. | |
| 5,357,956 A | 10/1994 | Nardella | |
| 5,364,393 A | 11/1994 | Auth et al. | |
| 5,370,649 A | 12/1994 | Gardetto et al. | |
| 5,374,261 A | 12/1994 | Yoon | |
| 5,374,283 A | 12/1994 | Flick | |
| 5,380,317 A | 1/1995 | Everett et al. | |
| 5,383,917 A | 1/1995 | Desai et al. | |
| 5,385,544 A | 1/1995 | Edwards et al. | |
| 5,395,311 A | 3/1995 | Andrews | |
| 5,405,322 A | 4/1995 | Lennox et al. | |
| 5,407,071 A | 4/1995 | Lawhon et al. | |
| 5,423,808 A | 6/1995 | Edwards et al. | |
| 5,433,708 A | 7/1995 | Nichols et al. | |
| 5,437,629 A | 8/1995 | Goldrath | |
| 5,443,470 A | 8/1995 | Stern et al. | |
| 5,451,204 A | 9/1995 | Yoon | |
| 5,474,089 A | 12/1995 | Waynant | |
| 5,484,400 A | 1/1996 | Edwards et al. | |
| 5,498,261 A | 3/1996 | Strul | |
| 5,505,730 A | 4/1996 | Edwards | |
| 5,507,743 A | 4/1996 | Edwards et al. | |
| 5,514,091 A | 5/1996 | Yoon | |
| 5,540,655 A | 7/1996 | Edwards et al. | |
| 5,540,681 A | 7/1996 | Strul et al. | |
| 5,540,684 A * | 7/1996 | Hassler, Jr. | 606/40 |
| 5,542,916 A | 8/1996 | Hirsch et al. | |
| 5,558,672 A | 9/1996 | Edwards et al. | |
| 5,562,703 A | 10/1996 | Desai | |
| 5,562,720 A | 10/1996 | Stern et al. | |
| 5,573,533 A | 11/1996 | Strul | |
| 5,575,788 A | 11/1996 | Baker et al. | |
| 5,588,961 A | 12/1996 | Leone et al. | |
| 5,593,404 A | 1/1997 | Costello et al. | |
| 5,599,345 A | 2/1997 | Edwards et al. | |
| 5,599,346 A | 2/1997 | Edwards et al. | |
| 5,609,598 A | 3/1997 | Laufer et al. | |
| 5,613,950 A | 3/1997 | Yoon | |
| 5,620,481 A | 4/1997 | Desai et al. | |
| 5,649,924 A | 7/1997 | Everett et al. | |
| 5,656,013 A | 8/1997 | Yoon | |
| 5,658,316 A | 8/1997 | Lamond et al. | |
| 5,667,520 A | 9/1997 | Bonutti | |
| 5,697,882 A | 12/1997 | Eggers et al. | |
| 5,702,438 A | 12/1997 | Avitall | |
| 5,716,343 A | 2/1998 | Kriesel et al. | |
| 5,722,975 A | 3/1998 | Edwards et al. | |
| 5,730,136 A | 3/1998 | Laufer et al. | |
| 5,730,725 A | 3/1998 | Yoon | |
| 5,733,252 A | 3/1998 | Yoon | |
| 5,769,880 A | 6/1998 | Truckai et al. | |
| 5,779,698 A | 7/1998 | Clayman et al. | |
| 5,797,903 A | 8/1998 | Swanson et al. | |
| 5,800,482 A | 9/1998 | Pomeranz et al. | |
| 5,807,389 A | 9/1998 | Gardetto et al. | |
| 5,810,847 A | 9/1998 | Laufer et al. | |
| 5,827,271 A * | 10/1998 | Buysse et al. | 606/40 |
| 5,827,273 A | 10/1998 | Edwards | |
| 5,843,026 A | 12/1998 | Edwards et al. | |
| 5,843,121 A | 12/1998 | Yoon | |
| 5,846,238 A | 12/1998 | Jackson et al. | |
| 5,865,788 A | 2/1999 | Edwards et al. | |
| 5,871,469 A | 2/1999 | Eggers et al. | |
| 5,879,348 A | 3/1999 | Owens et al. | |
| 5,885,601 A | 3/1999 | Sokal | |
| 5,888,198 A | 3/1999 | Eggers et al. | |
| 5,891,134 A | 4/1999 | Goble et al. | |
| 5,891,136 A | 4/1999 | McGee et al. | |
| 5,897,551 A | 4/1999 | Everett et al. | |
| 5,897,553 A | 4/1999 | Mulier et al. | |
| 5,935,123 A | 8/1999 | Edwards et al. | |
| 5,935,137 A | 8/1999 | Saadat et al. | |
| 5,938,660 A | 8/1999 | Swartz et al. | |
| 5,954,715 A | 9/1999 | Harrington et al. | |
| 5,954,717 A | 9/1999 | Behl et al. | |
| 5,979,446 A | 11/1999 | Loy | |
| 5,997,534 A | 12/1999 | Tu et al. | |
| 6,002,968 A | 12/1999 | Edwards | |
| 6,014,589 A | 1/2000 | Farley et al. | |
| 6,033,397 A | 3/2000 | Laufer et al. | |
| 6,036,687 A | 3/2000 | Laufer et al. | |
| 6,041,260 A | 3/2000 | Stern et al. | |
| 6,042,596 A | 3/2000 | Bonutti | |
| 6,047,700 A | 4/2000 | Eggers et al. | |
| 6,066,139 A | 5/2000 | Ryan et al. | |
| 6,068,613 A | 5/2000 | Kriesel et al. | |

| | | |
|---|---|---|
| 6,068,626 A | 5/2000 | Harrington et al. |
| 6,071,277 A | 6/2000 | Farley et al. |
| 6,074,386 A | 6/2000 | Goble et al. |
| 6,077,257 A | 6/2000 | Edwards et al. |
| 6,090,106 A * | 7/2000 | Goble et al. ............ 606/41 |
| 6,096,052 A | 8/2000 | Callister et al. |
| 6,112,123 A | 8/2000 | Kelleher et al. |
| 6,117,101 A | 9/2000 | Diederich et al. |
| 6,123,702 A | 9/2000 | Swanson et al. |
| 6,135,997 A | 10/2000 | Laufer et al. |
| 6,139,527 A | 10/2000 | Laufer et al. |
| 6,139,546 A | 10/2000 | Koenig et al. |
| 6,152,899 A | 11/2000 | Farley et al. |
| 6,159,207 A | 12/2000 | Yoon |
| 6,162,216 A * | 12/2000 | Guziak et al. ............ 606/34 |
| 6,164,280 A | 12/2000 | Everett et al. |
| 6,165,172 A | 12/2000 | Farley et al. |
| 6,179,832 B1 | 1/2001 | Jones et al. |
| 6,183,468 B1 | 2/2001 | Swanson |
| 6,193,713 B1 | 2/2001 | Geistert et al. |
| 6,197,025 B1 | 3/2001 | Grossi et al. |
| 6,200,312 B1 | 3/2001 | Zikorus et al. |
| 6,231,496 B1 | 5/2001 | Wilk et al. |
| 6,231,507 B1 | 5/2001 | Zikorus et al. |
| 6,234,178 B1 | 5/2001 | Goble |
| 6,237,606 B1 | 5/2001 | Zikorus et al. |
| 6,238,393 B1 | 5/2001 | Mulier et al. |
| 6,245,065 B1 | 6/2001 | Panescu et al. |
| 6,245,090 B1 | 6/2001 | Gilson et al. |
| 6,254,601 B1 | 7/2001 | Burbank et al. |
| 6,258,084 B1 | 7/2001 | Goldman et al. |
| 6,258,085 B1 | 7/2001 | Eggleston |
| 6,263,248 B1 | 7/2001 | Farley et al. |
| 6,277,089 B1 | 8/2001 | Yoon |
| 6,293,942 B1 | 9/2001 | Goble et al. |
| 6,296,639 B1 | 10/2001 | Truckai et al. |
| 6,309,384 B1 | 10/2001 | Harrington et al. |
| 6,315,776 B1 | 11/2001 | Edwards et al. |
| 6,322,559 B1 | 11/2001 | Daulton et al. |
| 6,346,102 B1 | 2/2002 | Harrington et al. |
| 6,352,549 B1 | 3/2002 | Everett |
| 6,364,877 B1 | 4/2002 | Goble et al. |
| 6,369,465 B1 | 4/2002 | Swanson |
| 6,395,012 B1 | 5/2002 | Yoon et al. |
| 6,398,780 B1 | 6/2002 | Farley et al. |
| 6,402,742 B1 | 6/2002 | Blewett et al. |
| 6,428,537 B1 | 8/2002 | Swanson |
| 6,432,116 B1 | 8/2002 | Callister et al. |
| 6,451,015 B1 | 9/2002 | Rittman et al. |
| 6,475,213 B1 | 11/2002 | Whayne et al. |
| 6,485,487 B1 | 11/2002 | Sherman |
| 6,485,500 B1 | 11/2002 | Kokish et al. |
| 6,490,474 B1 | 12/2002 | Willis et al. |
| 6,508,815 B1 | 1/2003 | Strul et al. |
| 6,554,780 B1 | 4/2003 | Sampson et al. |
| 6,663,626 B2 | 12/2003 | Truckai et al. |
| 6,679,269 B2 | 1/2004 | Swanson |
| 6,712,810 B2 | 3/2004 | Harrington et al. |
| 6,712,815 B2 | 3/2004 | Sampson et al. |
| 6,726,682 B2 | 4/2004 | Harrington et al. |
| 6,743,184 B2 | 6/2004 | Sampson et al. |
| 6,764,488 B1 | 7/2004 | Burbank et al. |
| 6,813,520 B2 | 11/2004 | Truckai et al. |
| 6,964,274 B1 | 11/2005 | Ryan et al. |
| 7,074,217 B2 | 7/2006 | Strul et al. |
| 7,407,502 B2 | 8/2008 | Strul et al. |
| 7,512,445 B2 | 3/2009 | Truckai et al. |
| 7,604,633 B2 | 10/2009 | Truckai et al. |
| 7,717,909 B2 | 5/2010 | Strul et al. |
| 7,731,712 B2 | 6/2010 | Sampson et al. |
| 7,846,160 B2 | 12/2010 | Payne et al. |
| 2001/0041900 A1 | 11/2001 | Callister et al. |
| 2002/0022870 A1 | 2/2002 | Truckai et al. |
| 2002/0029051 A1 | 3/2002 | Callister et al. |
| 2002/0072499 A1 | 6/2002 | Clagett |
| 2002/0072745 A1 | 6/2002 | Truckai et al. |
| 2002/0128649 A1 * | 9/2002 | Bacher et al. ............ 606/46 |
| 2002/0177846 A1 | 11/2002 | Mulier et al. |
| 2003/0093101 A1 | 5/2003 | O'Heeron et al. |
| 2003/0130711 A1 | 7/2003 | Pearson |
| 2003/0199863 A1 | 10/2003 | Swanson |
| 2004/0054368 A1 | 3/2004 | Truckai et al. |
| 2004/0118166 A1 | 6/2004 | Huang et al. |
| 2004/0172051 A1 | 9/2004 | Ravikumar |
| 2004/0204720 A1 | 10/2004 | Harrington et al. |
| 2004/0255958 A1 | 12/2004 | Harrington et al. |
| 2005/0085880 A1 | 4/2005 | Truckai et al. |
| 2005/0155608 A1 | 7/2005 | Pavcnik et al. |
| 2005/0217680 A1 | 10/2005 | Callister et al. |
| 2006/0095032 A1 * | 5/2006 | Jackson et al. ............ 606/41 |
| 2008/0071269 A1 | 3/2008 | Hilario et al. |
| 2010/0036372 A1 | 2/2010 | Truckai et al. |
| 2010/0217256 A1 | 8/2010 | Strul et al. |
| 2012/0179155 A1 | 7/2012 | Strul et al. |

FOREIGN PATENT DOCUMENTS

| | | |
|---|---|---|
| DE | 4001086 | 1/1990 |
| EP | 0 056 178 A1 | 4/1981 |
| EP | 0 584 930 A1 | 7/1993 |
| EP | 1 400 182 | 6/2004 |
| FR | 774.550 | 9/1934 |
| FR | 70.43012 | 6/1972 |
| FR | 2115706 | 7/1972 |
| GB | 2317566 | 1/1998 |
| JP | 48-67586 | 9/1973 |
| JP | 58-32756 | 2/1983 |
| JP | 63-318934 | 12/1988 |
| WO | WO 92/19145 | 11/1992 |
| WO | WO 94/00178 | 1/1994 |
| WO | WO 94/07445 | 4/1994 |
| WO | WO 94/10948 | 5/1994 |
| WO | WO 94/23794 | 10/1994 |
| WO | WO 95/04385 | 2/1995 |
| WO | WO 95/05869 | 3/1995 |
| WO | WO 95/07664 | 3/1995 |
| WO | WO 95/10326 | 4/1995 |
| WO | 96/00042 | 1/1996 |
| WO | 97/12569 | 4/1997 |
| WO | 97/41785 | 11/1997 |
| WO | 98/38932 | 9/1998 |
| WO | WO 99/58070 | 11/1999 |
| WO | WO 01/97897 | 12/2001 |

OTHER PUBLICATIONS

C. Nibley et al., "Prevention of Impedance Rise During Radiofrequency Current Catheter Ablation by Intra-Electrode Tip Chilling," *Circulation* [Abstracts From the 67th Scientific Sessions, Dallas Convention Center, Dallas, Texas, Nov. 14-17, 1994], vol. 90, No. 4, Part 2, Oct. 1994, p. 460.

W.M. Jackman et al., "Radiofrequency Current Directed Across the Mitral Anulus With a Bipolar Epicardial-Endocardial Catheter Electrode Configuration in Dogs," *Circulation*, vol. 78, No. 5, Nov. 1988, pp. 1288-1298.

"Essure: the non-incisional approach to permanent birth control", Patient Information Booklet, ©2004 by Conceptus Incorporated.

"Tubal Ligation—Fimbriectomy: Tubal Reversal is Possible after Fimbriectomy" Datasheet [on-line] Chapel Hill Tubal Reversal Center, 2004 [retrieved on Oct. 19, 2004] Retrieved from the Internet: <URL:http://www.tubal-reversal.net/print/printer-friendly-tubal_ligation_fimbriectomy.htm>.

"Tubal Ligation and Resection: Tubal Ligation by Parkland and Irving Methods" Datasheet [on-line] Chapel Hill Tubal Reversal Center, 2004 [retrieved on Oct. 19, 2004] Retrieved from the Interent: <URL: http://www.tubal-reversal.net/print/printer-friendly-tubal_ligation_resection.htm>.

"Tubal Ligation—Tubal Ring or Clip: Tubal Ligation with Tubal Rings or Tubal Clips" Datasheet [on-line] Chapel Hill Tubal Reversal Center, 2004 [retrieved Oct. 19, 2004] Retrieved from the Internet: <URL: http://www.tubal-reversal.net/tubal_ligation-tubal_ring-tubal_clip.htm>.

"Tubal Ligation—Pomeroy Technique: Pomeroy Tubal Ligation and Resection" Datasheet [on-line] Chapel Hill Tubal Reversal Center, 2004 [retrieved Oct. 19, 2004] Retrieved from the Internet: <http://www.tubal-reversal.net/print/printer-friendly-tubal_ligation_Pomeroy.htm >.

"Tubal Ligation Methods: Coagulation Methods of Tubal Ligation" Datasheet [on-line] Chapel Hill Tubal Reversal Center, 2004, [retrieved Oct. 19, 2004] Retrieved from the Internet: <http://www.tubal-reversal.net/tubal_ligation_coagulation.htm >.

"Essure, Permanent Birth Control by Conceptus: What is Essure?" Product Information Sheet [on-line] [retrieved Oct. 19, 2004] Retrieved from the Internet: <URL: http://www.essure.com/consumer/c_what_is_essure.aspx>.

METI-MyriadLase, SteriLase, Powerpoint Presentation, published at least as of Jun. 13, 2006, 6 pp.

Adiana options for women—how it works. (Dec. 31, 2005). Retrieved from http://web.archive.org/web/20051124001429/www.adiana.com/products.sub.--h- ow.php.

First Request for *Ex Partes* Reexamination of U.S. Patent No. 5,769,880, filed Jul. 27, 1999.

Second Request for *Ex Partes* Reexamination of U.S. Patent No. 5,769,880, filed Nov. 22, 2000.

* cited by examiner

POWER RAMPING DURING RF ABLATION

TECHNICAL FIELD

This invention relates to a medical procedure.

BACKGROUND

Ablation of the interior lining of a body organ is a procedure that involves heating the organ lining to temperatures that destroy the cells of the lining or coagulate tissue proteins for hemostasis. Such a procedure may be performed as a treatment to one of many conditions, such as chronic bleeding of the endometrial layer of the uterus or abnormalities of the mucosal layer of the gallbladder. Existing techniques for effecting ablation include circulation of heated fluid inside the organ (either directly or inside a balloon), laser treatment of the organ lining, and resistive heating using application of RF energy to the tissue to be ablated.

An example of resistive heating using application of RF energy to the tissue is described in U.S. Pat. No. 5,769,880, entitled "Moisture Transport System for Contact Electrocoagulation", issued to Truckai, et al, on Jun. 23, 1998. A system for transporting moisture away from the ablation site is described therein. A build-up of fluid at the ablation site can decrease impedance at the electrode/tissue interface effecting the depth of tissue destruction and efficiency of the procedure.

In some prior art RF devices, fluid drawn from the tissue creates a path of conductivity through which current traveling through the electrodes will flow. This can prevent the current from traveling into the tissue to be ablated. Moreover, the presence of this current path around the electrodes causes current to be continuously drawn from the electrodes. The current heats the liquid drawn from the tissue and thus turns the ablation process into a passive heating method in which the heated liquid around the electrodes causes thermal ablation to continue well beyond the desired ablation depths.

SUMMARY

The invention described herein relates to a medical procedure. In general, in one aspect, the invention features a method for tissue ablation. An RF applicator including an electrode carrier with one or more bipolar electrodes thereon is positioned at a target tissue site for tissue ablation. A current at an initial current level is passed through the one or more bipolar electrodes to the target tissue site to apply an initial power density to destroy tissue for an initial time period. A vacuum source in fluid communication with the RF applicator is employed to remove moisture generated during ablation away from the target tissue site. After the initial time period, the power density is ramped up by increasing the current passed through the one or more bipolar electrodes to the target tissue site for a second time period.

Implementations of the invention can include one or more of the following features. Ramping up the power density can include steadily increasing the current over the second time period. Alternatively, ramping up the power density can include suddenly increasing the current from the initial current level to a second current level and applying the second current level for the second time period. The method can further include monitoring an impedance level at an interface between the target tissue site and the RF applicator, where the initial time period is a time period after which a threshold decrease in the impedance level from an initial impedance level is detected. The second time period can be a time period beginning when the threshold decrease in impedance level is detected and ending when the impedance level is detected as having returned to substantially the initial impedance level. After the second time period, the power density can be decreased to the initial power density. In one implementation, after decreasing the power density to the initial power density, the power density can be steadily increased over a third time period.

In one implementation, the target tissue site is a tubal ostium in a female uterine cavity, the initial power density is approximately 5 watts per square centimeter, the decrease in impedance level detected is a decrease of approximately 25%, and the power density is increased during the second time period at a rate of approximately 1 watt per square centimeter per second. In another implementation, the target tissue site is a tubal ostium in a female uterine cavity, the initial power density is approximately 5 watts per square centimeter, the decrease in impedance level detected is a decrease of approximately 33%, and the power density is increased during the second time period at a rate of approximately 2.5 watts per square centimeter per second. In yet another implementation, the target tissue site is a tubal ostium in a female uterine cavity, the initial power density is approximately 5 watts per square centimeter, the decrease in impedance level detected is a decrease of approximately 50%, and the power density is increased during the second time period to a level of approximately 10 to 15 watts per square centimeter.

The initial time period can be determined empirically as a time period after which an initial depth of tissue destruction has been achieved. In one implementation, the target tissue site is a tubal ostium in a female uterine cavity, the initial power density is approximately 5 watts per square centimeter, the initial time period is between approximately 45 and 60 seconds, the power density is increased during the second time period at a rate of approximately 1 watt per square centimeter per second, and the second time period is between approximately 5 and 10 seconds. In another implementation, the target tissue site is a tubal ostium in a female uterine cavity, the initial power density is approximately 5 watts per square centimeter, the initial time period is between approximately 10 and 60 seconds, the power density is increased during the second time period at a rate of approximately 0.5 to 2.5 watts per square centimeter per second, and the second time period is between approximately 5 and 10 seconds.

Implementations of the invention can feature one or more of the following advantages. The techniques for controlling the power density to an ablation site provide the benefit of starting out with a power density low enough to obtain the desired depth of ablation, while ramping up the power density at the appropriate time to address any fluid migration that may occur as the ablation progresses.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Figure 1:
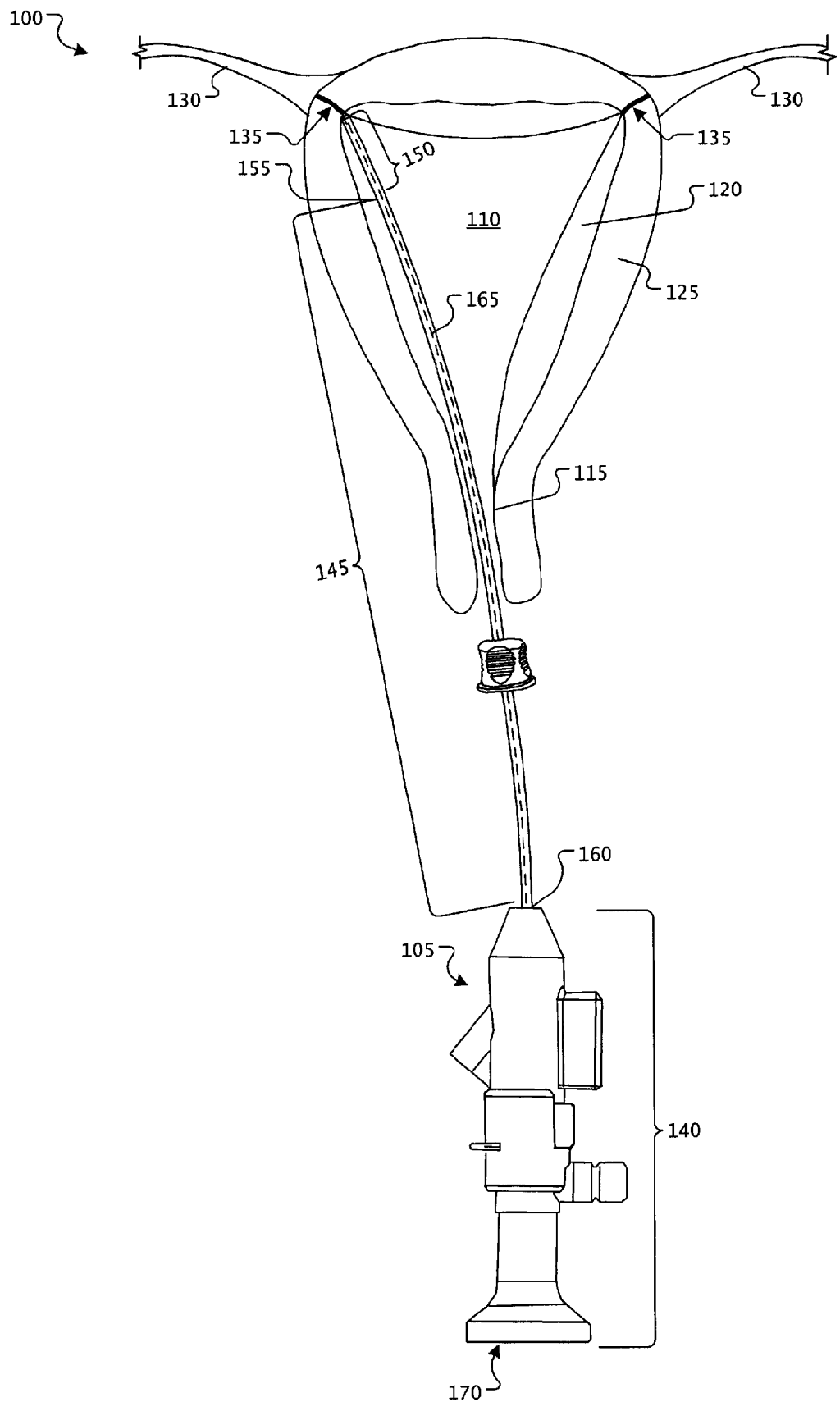
FIG. 1 shows an ablation device positioned in a uterus.

A technique for tissue ablation using resistive heating and a moisture transport system is described. An RF applicator including an electrode carrier with one or more bipolar electrodes thereon is positioned at a target tissue site for tissue ablation. A current at an initial current level is passed through the one or more bipolar electrodes to the target tissue site to apply an initial power density to destroy tissue for an initial time period. A vacuum source in fluid communication with the RF applicator is employed to remove moisture generated during ablation away from the target tissue site. After the initial time period, the power density is ramped up by increasing the current passed through the one or more bipolar electrodes to the target tissue site. The ramped up power is applied for a second time period.

Because, even with the vacuum source employed, fluid can migrate into the region of the electrode/tissue interface, impedance levels at the interface can drop. If the excess fluid is not removed, it may create a path of conductivity through which the current traveling through the electrodes will flow. This can prevent the current from traveling into the tissue to be ablated. Moreover, the presence of this current path around the electrodes can cause current to be continuously drawn from the electrodes. The current heats the liquid drawn from the tissue and thus can turn the ablation process into a passive heating method, in which the heated liquid around the electrodes causes thermal ablation to continue well beyond the desired ablations depths.

Power density is inversely proportional to the depth of tissue destruction. As such, a relatively low power density is generally used to achieve desired depths of destruction. Ablated tissue becomes dehydrated and therefore decreases in conductivity. By shunting moisture away from the ablation site and preventing fluid build-up, a fluid conductor at the ablation area during use of the ablation device can be avoided. When ablation reaches a desired depth, the impedance at the electrode/tissue interface becomes sufficiently high to stop or nearly stop the flow of current into the tissue. The RF ablation thereby stops and thermal ablation does not occur in significant amounts. By equipping the RF generator with an impedance monitor, the operator of the ablation device can monitor the impedance at the electrode/tissue interface and will know that ablation has self-terminated once the impedance rises to a certain level and then remains fairly constant. In one implementation, the RF generator can be configured to automatically shut-off RF power once the impedance rises to the certain level.

However, in some ablation procedures, it can be difficult to avoid fluid migration into the ablation area, even with the use of a moisture transport system. If excess fluid does migrate into the electrode/tissue interface region, ramping up the power density is an effective way to handle the excess fluid and drive up the tissue impedance. A higher power density can vaporize the fluid easily and recover the impedance signal, whereas a lower power density can languish, unable to manage the fluid in a timely fashion, leading to abnormally long procedure times and tissue destruction deeper than desired. Techniques are described herein for determining at what point in an ablation procedure to ramp up power density to deal with excess fluid, while still achieving the desired depth of destruction.

In one implementation, a time-based function is used. That is, after a pre-determined initial time period the power density is increased, either suddenly or gradually, and the increased (or increasing) power density is applied for a second time period. In one implementation, the initial and second time periods can be determined empirically. For example, an initial power density can be applied to an experimental target tissue site for varying time periods, a fluid is then intentionally introduced into the target tissue site and the power density ramped by varying amounts for varying time periods. By experimenting with the initial time period, initial power density, power ramp up and second time period, while monitoring the depth of tissue destruction, the desired time periods and power levels can be determined.

In another implementation, an impedance-based function is used. That is, the impedance at the electrode/tissue interface is monitored. Upon detecting a decrease in the impedance by a threshold amount, which can indicate the presence of a fluid layer, the power density can be ramped up either suddenly or gradually. A sudden ramp-up is generally preferred for a sudden, relatively large drop in impedance, while a gradual ramp-up is preferred otherwise, as shall be described in further detail below.

The power ramping techniques described herein can be used in various tissue ablation procedures. For illustrative purposes, one implementation involving tissue ablation in the region of a tubal ostium in a female for the purpose of fallopian tubal occlusion is described. A medical device to perform the procedure includes an RF applicator head configured to position within the tubal ostium. Examples of such medical devices are described in U.S. patent application Ser. No. 11/019,580, entitled "Method and System for Transcervical Tubal Occlusion", filed Dec. 20, 2004, by Sampson, et al and in U.S. patent application Ser. No. 11/532,886, entitled "Curved Endoscopic Medical Device", filed Sep. 18, 2006, by Sampson et al, and the entire contents of both applications are hereby incorporated by reference. To illustrate the techniques for power ramping described herein, reference shall be made to medical devices configured for tubal occlusion, however, the power ramping techniques are not limited to such a medical procedure and can be applied in other ablation procedures.

Referring to FIG. 1, a schematic representation of a uterus 100 is shown with an ablation device 105 positioned within the uterus 100. The uterus includes a uterine cavity 110, and an internal os 115 both surrounded by uterine tissue, namely endometrial tissue 120 and myometrial tissue 125. The fallopian tubes 130 connect to the uterine cavity 110 at the tubal ostia 135.

The ablation device 105 generally includes three major components: a handle 140, a curved shaft 145, and a radio frequency (RF) applicator head 150. The curved shaft 145 includes a distal end 155, a proximal end 160, and a hollow central interior 165. The curved shaft 145 is a substantially rigid member configured with a curve to facilitate the advancement of the distal end 155 through a body cavity to a region of tissue to be ablated. The central interior 165 of the curved shaft 145 can include one or more lumens. For example, in one implementation, the central interior 165 includes a lumen that can be operated so as to couple a vacuum source to the RF applicator head 150. The application of vacuum can be used to draw moisture away from one or more electrodes included in the RF applicator head 150 at the electrode/tissue interface.

Additionally, a lumen (either the same lumen that couples to a vacuum source or a different lumen) can be configured to receive a curved hysteroscope. Further, the handle 140 is configured to couple the ablation device 105 to the curved hysteroscope, which is received via a port 170, and to a coupling assembly to couple the ablation device to a controller.

The RF applicator head 150 is positioned at the distal end 155 of the curved shaft 145 and includes an electrode carrier having one or more bipolar electrodes. One or more electrical conductors extend from the RF applicator head 150 to the proximal end 160 of the curved shaft 145 and electrically couple the RF applicator head 150 to a controller. The controller can be operated so as to control the delivery of RF energy to the one or more bipolar electrodes.

In the particular implementation shown in FIG. 1, the ablation device 100 is configured to facilitate entry into the uterine cavity 110 to occlude one or more of the tubal ostia 135. Occluding the tubal ostia 135 prevents sperm from entering the fallopian tubes 130 and fertilizing an egg, thereby sterilizing the female.

The RF applicator head 150 is introduced transcervically into the uterine cavity and positioned at a tubal ostium 135. Transmitting RF energy through the RF applicator head 150 ablates the uterine tissue 120, 125 and the tissue within the tubal ostium 135. Following the destruction of the tissue at the tubal ostium 135, the healing response occludes the tubal ostium 135 and the adjacent portion of the fallopian tube 130 resulting in sterilization.

Tissue ablation can occur by positioning the RF applicator head 150 at a target tissue site and by passing a current at an initial current level through the one or more bipolar electrodes in the RF applicator head 150 to the target tissue site. The current is passed at an initial current level to the target tissue site such that the tissue is destroyed by applying an initial RF power density for an initial (i.e., first) time period. As the tissue is destroyed by the RF energy, fluid is released by the tissue undergoing ablation. The moisture can be withdrawn from the electrode/tissue interface by the application of vacuum. However, fluid may migrate from another area of the uterine cavity or bleeding near the region may occur. Thus, even with the application of vacuum, over time a layer of fluid can form near the electrodes and decrease the impedance level at the electrode/tissue interface. Increasing the RF power density can help to vaporize the excess fluid thereby increasing the impedance. Ramping up the RF power density can be either abrupt or gradual.

Figure 2A:
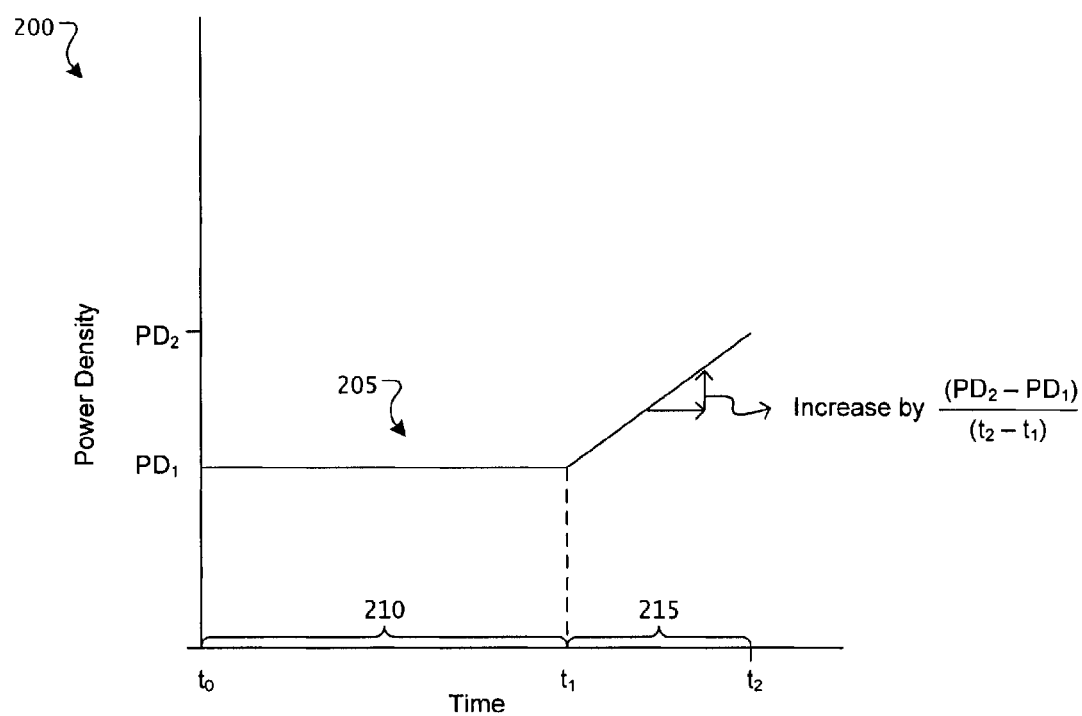
FIG. 2A shows a power density delivery profile.
Figure 2B:
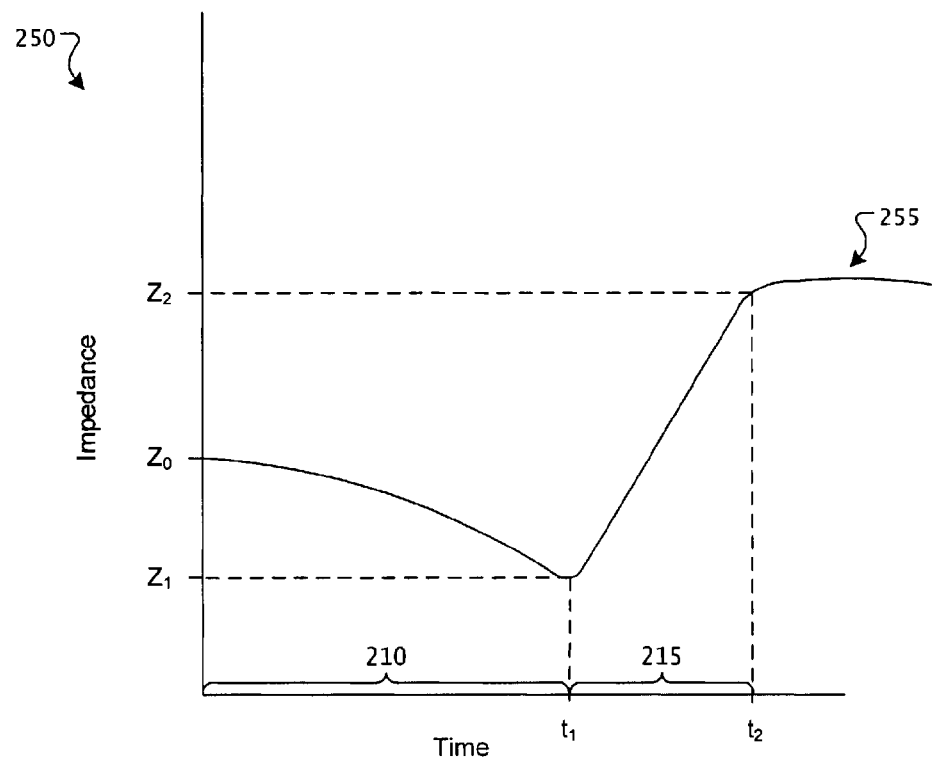
FIG. 2B shows an impedance profile corresponding to the power density delivery profile of FIG. 2A.

In one embodiment, ramping up the RF power density includes steadily or gradually increasing the current over the second time period. Determining when to begin the power ramp-up, i.e., determining the value of the initial time period, and the amount by which to ramp-up, as mentioned above in one implementation is according to a time-based function and in another implementation is according to an impedance-based function. Referring to FIGS. 2A and 2B, plots of an RF power density profile 205 and a corresponding impedance profile 255 are shown. In the implementation shown in FIG. 2A, the RF power density applied to the tissue ablation site is substantially constant at value $PD_1$ for the duration of a first time period 210 of n seconds, where $n=t_1-t_0$. At the end of the first time period 210, the RF power density is ramped up at a substantially constant and gradual rate to a value $PD_2$ for the duration of a second time period 215. In the implementation shown, the power ramping rate is linear, however, in other implementations, the power can be ramped at a non-linear rate.

The duration of the first time period 210, i.e., n seconds, is a time after which the impedance level at the electrode/tissue interface decreases to a threshold impedance of $Z_1$ or by a threshold percentage level to $Z_1$. As discussed above, the value of "n" can be determined either empirically, e.g., by experimentation, or by monitoring the impedance at the electrode/tissue interface. In either case, once the threshold impedance $Z_1$ has been reached, the power density is ramped up to vaporize excess fluid that has likely migrated to the electrode/tissue interface and caused the decrease in impedance. The RF power density applied for the duration of the second time period 215 is ramped up at a constant rate from $PD_1$ to $PD_2$. The rate of RF power density increase in the implementation shown can be calculated as: $(PD_2-PD_1)/(t_2-t_1)$.

The impedance profile 255 of FIG. 2B shows the effect on the impedance level at the electrode/tissue interface upon ramping up the power density. As fluid at the tissue ablation site is substantially vaporized by the increased power density and the tissue continues to undergo ablation, the impedance level increases. At a point in time $t_2$, the RF power is terminated, either based on the time period 215, which can be empirically determined, or based on the impedance level substantially flattening out at that point, indicating the tissue ablation process is complete.

By way of illustration, in the context of tissue ablation for the purpose of tubal occlusion, the values of power density relative to the monitored impedance level when carrying out the implementation shown in FIGS. 2A-B, while monitoring impedance levels, can be as set forth in the table below. These values are only illustrative of one implementation, and differing values can be appropriate. The depth of tissue destruction is dependent on factors other than power density, for example, electrode spacing, and thus if other factors are varied, the power density levels indicated below may change as well.

| Initial Power Density (watts/cm$^2$) | Drop in Impedance at $t_1$ | Rate of Power Density Increase ({watts/cm$^2$}/sec) |
|---|---|---|
| 5 | 25% | 1 |
| 5 | 33% | 2–3 |

In the implementation depicted in FIGS. 2A-B where the values of time period and power densities are determined empirically, i.e., rather than by monitoring impedance levels, the values of time and power density in an application of tubal occlusion can be as follows. The initial RF power density can be approximately 5 watts/cm$^2$ and the initial time period "n" can be between approximately 10 and 60 seconds. After the first time period, and for the duration of the second time period, the RF power density can be increased at a rate of approximately 0.5 to 2.5 watts/cm$^2$ per second. The duration of the second time period can be between approximately 5 and 10 seconds.

In a more specific example, the initial RF power density is approximately 5 watts/cm$^2$ and the initial time period is between approximately 45 and 60 seconds. After the first time period, and for the duration of the second time period, the RF power density is increased at a rate of approximately 1 watt/cm per second. The duration of the second time period is between approximately 5 and 10 seconds.

Figure 3A:
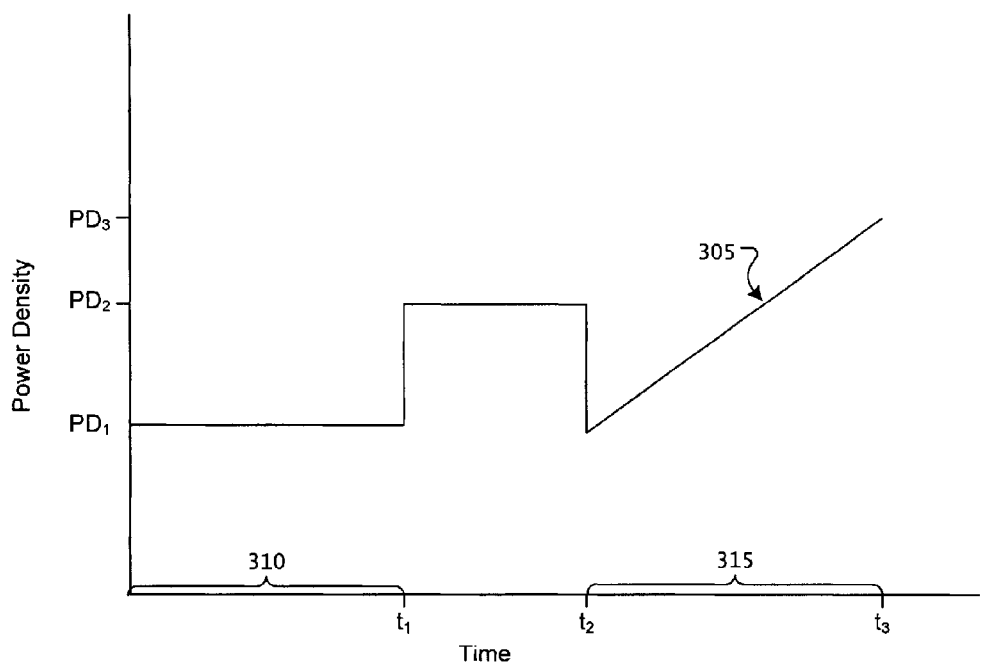
FIG. 3A shows a power density delivery profile.
Figure 3B:
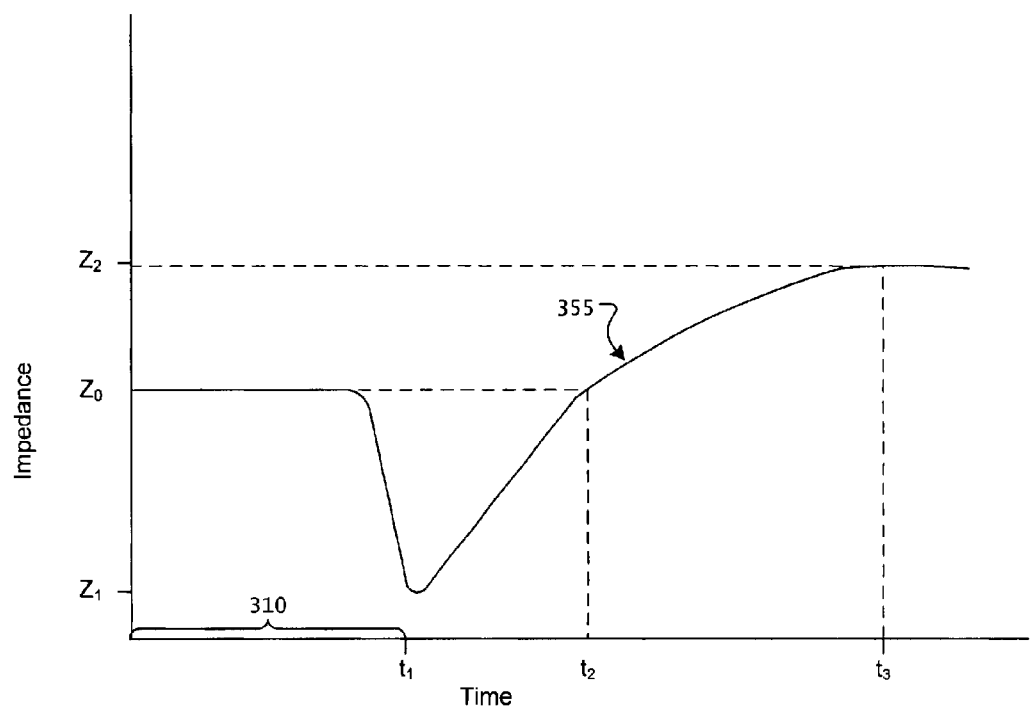
FIG. 3B shows an impedance profile corresponding to the power density delivery profile of FIG. 3A.

Referring to FIGS. 3A and 3B, plots of an RF power density profile 305 and a corresponding impedance profile 355 are shown. In this implementation, the RF power density applied to the tissue ablation site is substantially constant at $PD_1$ for first time period 310. At time t, there is a sudden and significant decrease in impedance from $Z_0$ to $Z_1$ as shown by the sharp drop in the curve 355. In response to the decrease in impedance, the RF power density is abruptly ramped up to a level $PD_2$. In one implementation, the level $PD_2$ is empirically determined in advance. The level $PD_2$ can be a function of the percentage in decrease of the impedance level.

In one implementation, the RF power density is held at the level $PD_2$ until the impedance increases to the level it was at prior to the sudden and significant decrease, i.e., $Z_0$. The RF power density is then returned to the initial level $PD_1$. In the implementation shown, the RF power density is then gradually ramped up for a time period 315 from $PD_2$ to $PD_3$. The gradual ramp up in RF power density can start immediately (as shown in FIG. 3A), or can start after another time period has passed. Once the impedance reaches a threshold high at $Z_3$ (and/or flattens out), the tissue ablation is complete and the RF power is terminated.

Figure 4A:
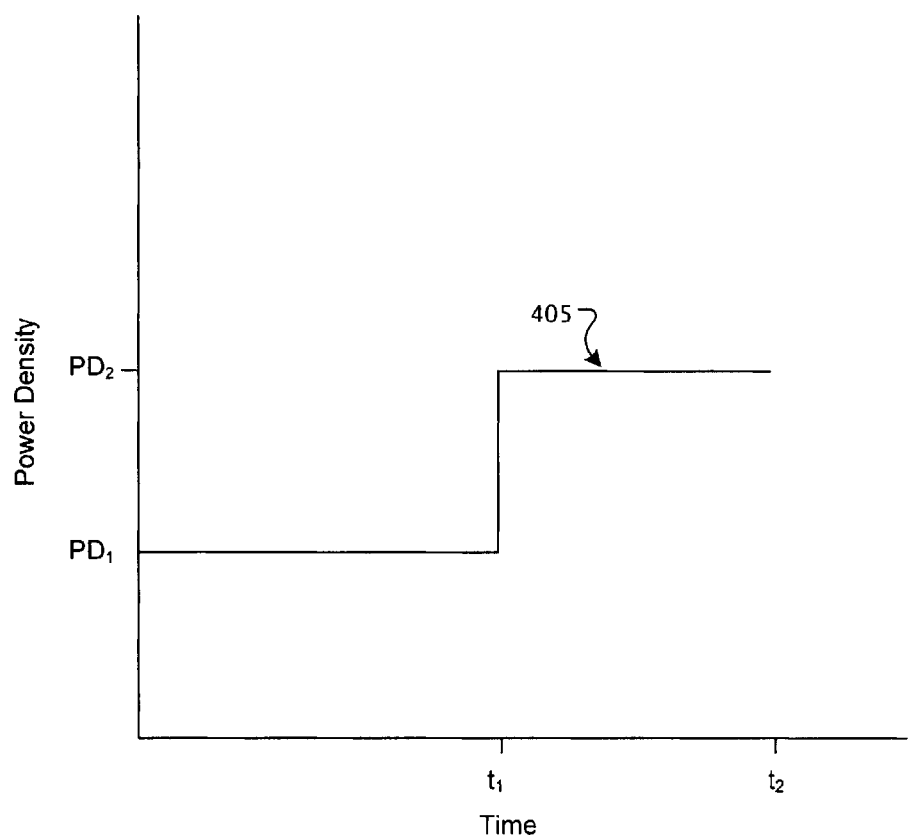
FIG. 4A shows a power density delivery profile.
Figure 4B:
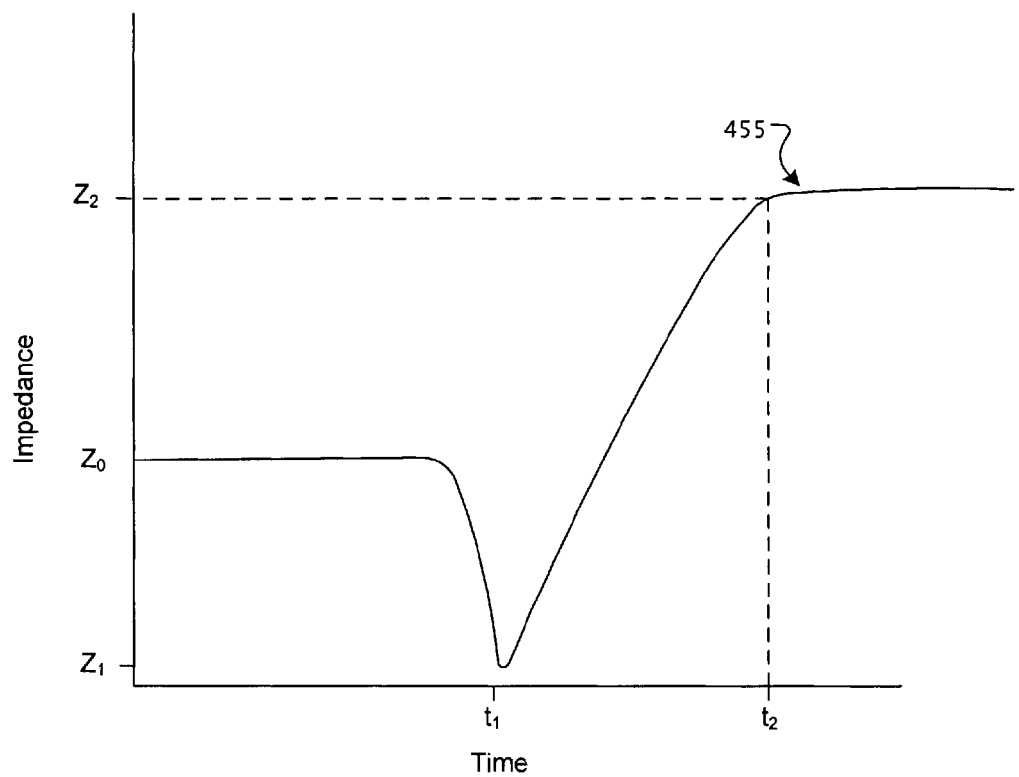
FIG. 4B shows an impedance profile corresponding to the power density delivery profile of FIG. 4A.

Referring to FIGS. 4A and 4B, plots of an RF power density profile 405 and an impedance profile 455 are shown. In this implementation, the RF power density is applied to the tissue ablation site at a substantially constant value (i.e., $PD_1$) for the duration of a first time period 410. At time $t_1$, the impedance level is detected as suddenly and significantly decreasing from $Z_0$ to $Z_1$. As discussed above in reference to FIGS. 3A and 3B, in response to the decrease in impedance, the RF power density is abruptly ramped up to a level $PD_2$. In this implementation, the RF power density is maintained at the level $PD_2$ until the impedance reaches a threshold high and/or flattens out at $Z_2$. At this point, the tissue ablation is complete and the delivery of RF power is terminated.

By way of illustration, in the context of tissue ablation for the purpose of tubal occlusion, the initial power density $PD_1$ can be approximately 5 watts/cm². Upon detecting a decrease in the impedance level by approximately 50% or more, the power density is ramped up to $PD_2$ which is in the range of approximately 10-15 watts/cm². In the implementation shown in FIGS. 3A-B, after the impedance level has returned to approximately the initial pre-drop level of $Z_0$, the power density is returned to $PD_1$ of approximately 5 watts/cm². Optionally, the power density can then be ramped up, either immediately or after a duration of time, at a rate of approximately 1 watt/cm² per second. These values are only illustrative of one implementation, and differing values can be appropriate. The depth of tissue destruction is dependent on factors other than power density, for example, electrode spacing, and thus if other factors are varied, the power density levels indicated below may change as well.

The delivery of RF power in the implementations shown in FIGS. 3A-B and 4A-B starts out at a density low enough such that the desired depths of ablation needed are obtained. The magnitude of power density is inversely proportional to the depth of tissue destruction. With all other variables fixed, a deeper ablation is obtained with a lower power density, and a shallower ablation is obtained with a higher power density. The spacing between the electrodes (i.e., the distance between the centers of adjacent electrodes) and the widths of the electrodes in the RF applicator head 150 can be selected so that ablation will reach predetermined depths within the tissue, particularly when maximum power is delivered through the electrodes. The maximum power is the level at which low impedance, and low voltage ablation can be achieved. The depth of ablation is also affected by the electrode density in the RF applicator head 150 and may be regulated by preselecting the amount of active electrode coverage. In one implementation, the electrode density in the RF applicator head 150 is approximately 10-20% density.

In other implementations, e.g., with differently configured electrodes or with differently desired depths of destruction, the power density levels and time periods will vary. However, whatever the RF power density and times, the technique of ramping up RF power density to deal with an unwanted fluid migration while performing tissue ablation with bipolar electrodes and a moisture transport system can be applied. Any fluid that migrates into the vicinity of the electrode, even under the influence of vacuum, will decrease the impedence at the tissue/electrode interface. The fluid can be vaporized to stabilize the impedance and then additional power ramping can be applied, depending on the desired result.

A number of embodiments of the invention have been described. Nevertheless, it will be understood that various modifications may be made without departing from the spirit and scope of the invention. Accordingly, other embodiments are within the scope of the following claims.

What is claimed is:

1. A method for tissue ablation comprising:
   positioning a radiofrequency (RF) applicator comprising an electrode carrier with one or more bipolar electrodes thereon at a target tissue site within a body cavity for ablating the interior lining of the body cavity;
   passing a current at an initial current level through the one or more bipolar electrodes to the target tissue site to apply an initial power density to destroy tissue, wherein power is applied at said initial current level for an initial time period;
   employing a vacuum source in fluid communication with the RF applicator to remove fluid generated during ablation away from the target tissue site, wherein excess fluid not removed by the vacuum source builds up at the target tissue site; and
   after the initial time period, ramping up the power density by increasing the current passed through the one or more bipolar electrodes to the target tissue site for a second time period, wherein the excess fluid build-up is vaporized during said second time period.

2. The method of claim 1, wherein ramping up the power density comprises steadily increasing the current over the second time period.

3. The method of claim 1, wherein ramping up the power density comprises suddenly increasing the current from the initial current level to a second current level and applying the second current level for the second time period.

4. The method of claim 1, further comprising:
   monitoring an impedance level at an interface between the target tissue site and the RF applicator; wherein the impedance is at an initial impedance level at the outset of passing the current and the initial time period ends when a threshold decrease in the impedance level below the initial impedance level is detected.

5. The method of claim 4, where the second time period begins when the threshold decrease in impedance level is detected and ends when the impedance level is detected as having returned to substantially the initial impedance level, the method further comprising:
   after the second time period ends, decreasing the power density to the initial power density.

6. The method of claim 5, further comprising: after decreasing the power density to the initial power density, steadily increasing the power density over a third time period.

7. The method of claim 4, wherein the target tissue site is a tubal ostium in a female uterine cavity; the initial power density is approximately 5 watts per square centimeter; the threshold decrease in the impedance level detected is a decrease of approximately 25%; and the power density is increased during the second time period at a rate of approximately 1 watt per square centimeter per second.

8. The method of claim 4, where: the target tissue site is a tubal ostium in a female uterine cavity; the initial power density is approximately 5 watts per square centimeter; the threshold decrease in the impedance level detected is a decrease of approximately 33%; and the power density is increased during the second time period at a rate of approximately 2.5 watts per square centimeter per second.

9. The method of claim 4, where: the target tissue site is a tubal ostium in a female uterine cavity; the initial power density is approximately 5 watts per square centimeter; the threshold decrease in the impedance level detected is a decrease of approximately 50%; and the power density is increased during the second time period to a level of approximately 10 to 15 watts per square centimeter.

10. The method of claim 1, where the initial time period is determined empirically as a time period after which an initial depth of tissue destruction has been achieved.

11. The method of claim 10, where: the target tissue site is a tubal ostium in a female uterine cavity; the initial power density is approximately 5 watts per square centimeter; the initial time period is between approximately 45 and 60 seconds; the power density is increased during the second time period at a rate of approximately 1 watt per square centimeter per second; and the second time period is between approximately 5 and 10 seconds.

12. The method of claim 10, where: the target tissue site is a tubal ostium in a female uterine cavity; the initial power density is approximately 5 watts per square centimeter; the initial time period is between approximately 10 and 60 seconds; the power density is increased during the second time period at a rate of approximately 0.5 to 2.5 watts per square centimeter per second; and the second time period is between approximately 5 and 10 seconds.

13. A method for tissue ablation comprising:
 positioning a radiofrequency (RF) applicator comprising an electrode carrier with one or more bipolar electrodes thereon at a target tissue site for tissue ablation;
 passing a current at an initial current level through the one or more bipolar electrodes to the target tissue site to apply an initial power density to destroy tissue, wherein power is applied at said initial current level for an initial time period;
 employing a vacuum source in fluid communication with the RF applicator to remove moisture generated during ablation away from the target tissue site, wherein excess fluid not removed by the vacuum source builds up at the target tissue site;
 monitoring an impedance level at an interface between the target tissue site and the RF applicator;
 detecting an impedance level decrease from an initial level detected at the outset of passing the current by a threshold amount;
 after the impedance level decrease has been detected, ramping up the power density by increasing the current passed through the one or more bipolar electrodes to the target tissue site for a second time period, wherein the excess fluid build-up is vaporized during said second time period.

\* \* \* \* \*